United States Patent [19]

Cairati et al.

[11] 4,181,629

[45] Jan. 1, 1980

[54] CATALYST FOR THE OXIDATION OF METHANOL TO FORMALDEHYDE AND A METHOD OF PREPARING THE CATALYST

[75] Inventors: Luciano Cairati, Cassano D'Adda; Lucio di Fiore, Milan, both of Italy

[73] Assignee: Euteco S.p.A., Milan, Italy

[21] Appl. No.: 916,691

[22] Filed: Jun. 19, 1978

[51] Int. Cl.$^2$ .................... B01J 21/04; B01J 21/08; B01J 23/88
[52] U.S. Cl. .................... 252/458; 252/465; 260/603 C
[58] Field of Search .................... 252/458, 465; 260/603 C

[56] References Cited

U.S. PATENT DOCUMENTS

3,975,302   8/1976   Courty et al. .................... 252/465 X

*Primary Examiner*—W. J. Shine
*Attorney, Agent, or Firm*—Sughrue, Rothwell, Mion, Zinn and Macpeak

[57] ABSTRACT

Catalyst for the oxidation of methanol to formaldehyde usable in the fluidized form in said oxidation, comprising iron and molybdenum oxides on a granular support, said support being a silica or an alumina having a specific surface area not exceeding 1 m$^2$/g and an overall pore volume not exceeding 0.2 ml/g and said oxides being present in the catalyst in an amount not exceeding 2 parts by weight for each 100 parts by weight of the support and in an atomic ratio between molybdenum and iron of from 1.5:1 to about 2.5:1.

11 Claims, No Drawings

CATALYST FOR THE OXIDATION OF METHANOL TO FORMALDEHYDE AND A METHOD OF PREPARING THE CATALYST

The present invention relates to the production of formaldehyde by catalytic oxidation of methanol.

More particularly, the invention relates to a novel catalyst which can be used in fluidized form and which is active and selective for such an oxidation reaction, and a process for the preparation of the catalyst.

In commercially known processes formaldehyde is obtained by dehydrogenation and oxidation of methanol on metallic silver, operating at high temperature and in deficiency of air, or else by oxidation of methanol in considerable excess of air on metal oxide catalysts, operating at relatively low temperatures (300°–400° C.).

The processes which use metal oxides as catalysts have, with respect to those using metallic silver, the advantages of higher yields in formaldehyde and almost complete methanol conversion. In consequence, one does not need to recover the unaltered methanol from the reaction products and aqueous solutions of formaldehyde which are substantially free of alcohol are obtained.

Metallic oxides suitable for this purpose are those of molybdenum and iron in which the $MoO_3/Fe_2O_3$ molar ratio may range within wide limits and in general from 1.5:1 to about 11:1.

Usually, these metallic oxides are not supported and are used in the preparation of methanol in the form of a fixed bed within the tubes of a tube bundle reactor. In fact, the oxidation of methanol is highly exothermic and the reaction heat is therefore removed by means of a cooling medium which is circulated, or else evaporated, on the outside of the tubes.

Recourse is also made in the art to the use of supported metallic oxides to obtain catalysts having higher mechanical characteristics, which can be used in fluidized form.

The use of a fluidized catalytic bed affords many advantages over the fixed bed technique and the supported catalysts are moreover more economical than the non-supported ones.

However, these supported catalysts have not been used on a commercial scale, mainly because it has not been possible until now to find supported catalysts in which the mechanical strength is combined with those characteristics of activity and selectivity which are required for a successful performance of catalytic oxidation of methanol.

These drawbacks are overcome, or at least greatly reduced, by means of the catalysts of the present invention, which are active and selective in the oxidation of methanol to formaldehyde and which can be used in fluidized form in said oxidation process, said catalysts comprising iron and molybdenum oxides deposited on a granular support.

Thus, the invention provides a catalyst which consists essentially of iron and molybdenum oxides on a granular support, said support being a silica or an alumina having a specific surface area not exceeding 1 $m^2/g$ and an overall pore volume not exceeding 0.2 ml/g and said oxides being present in the catalyst in an amount not exceeding 2 parts by weight for each 100 parts by weight of the support and in an atomic ratio between molybdenum and iron of from 1.5:1 to about 2.5:1 (corresponding to a molar ratio between molybdenum oxide ($MoO_3$) and iron oxide ($Fe_2O_3$) of from 3:1 to about 5:1).

Preferably, the support has a specific area of from 0.1 to 1 $m^2/g$ and an overall pore volume of from 0.1 to 0.2 ml/g. Moreover, the support is generally in the form of granules with a size of from 20 to 120 microns and preferably from 40 to 70 microns, this last range being most suited for fluidization.

The amount of iron and molybdenum oxides deposited on the support is preferably from 0.5 to 1 part by weight for each 100 parts by weight of the support. It is preferred that the amount of iron and molybdenum oxides deposited on the support be from 0.5 to 2 parts by weight for each 100 parts by weight of the support (this is equivalent to the overall content of iron and molybdenum being 0.5 to 2% by weight with respect to the weight of the support). Moreover, the molar ratio between molybdenum oxide and iron oxide is preferably maintained at a value higher than 3:1. In other words it is preferable to use a slight excess of molybdenum oxide with respect to the quantity which is stoichiometrically necessary for the formation of iron molybdate.

The present invention is essentially based on the discovery that the surface characteristics of the support have a noticeable influence on the behaviour of the catalysts in the process for the oxidation of methanol.

Thus, when the values of the specific surface area and the overall pore volume are higher than the limits indicated hereinbefore, important amounts of methanol are converted into total oxidation products. In other words, there is a decrease in selectivity of the catalyst; the higher the values of the specific surface area and overall pore volume, the lower is the selectivity.

This influence of the surface characteristics has been experimentally ascertained by flowing through the fluidized support, free from iron and molybdenum oxides, a gaseous mixture containing methanol and oxygen, maintaining the residence time and the temperature at values which are typically used for the oxidation of methanol into formaldehyde. It was thus ascertained that when using supports with a specific surface area not exceeding 1 $m^2/g$ and an overall pore volume not exceeding 0.2 ml/g, the methanol issuing from the bed of fluidized particles was practically unaltered, the degree of combustion being negligibly low. On the contrary, the combustion becomes more and more important as the values of the aforesaid surface characteristics are increased.

According to the present invention, the amount of iron and molybdenum oxides deposited on the support is also critical. The use of metal oxides in amount exceeding 2 parts by weight for each 100 parts by weight of the support leads to undesired phenomena identical with those which are ascertained when the specific surface area and the overall pore volume are increased. It was also ascertained that when the amount of iron and molybdenum oxides is kept within the range shown, it is possible to confer on the catalyst a relatively high mechanical strength, which is practically identical with that of the support used. Moreover, these catalysts are free from a tendency to give off powders; therefore, they can be used on a commercial scale for long periods of time.

The catalysts of the present invention may be prepared by a process which comprises:

impregnating granular silica or alumina, having the surface characteristics previously described, with an aqueous solution of decomposable salts of iron and molybdenum;

drying the thus impregnated support at a temperature not exceeding about 120° C.;

calcining the thus dried product in an oxidizing atmosphere at a temperature of from 300° to 500° C., and preferably from 350° to 450° C.

The support is preferably silica, especially microspheroidal silica which is easily available on the market. Generally, this silica is not endowed with the surface characteristics which are required for use in the catalyst of the invention and is therefore submitted to a thermal treatment at high temperatures, generally at temperatures higher than about 1000° C.

It is also possible to impregnate the silica beforehand with a decomposable alkali metal salt, especially a salt of sodium such as sodium carbonate. This expedient permits shorter times and/or lower temperatures to be used for the thermal treatment. In each case the calcining periods must be such as to reduce the specific surface area and the overall pore volume to values not exceeding 1 m$^2$/g and 0.2 ml/g, respectively.

The salts of molybdenum and iron are chosen from those which are decomposed into oxides under the calcining conditions, such as ammonium paramolybdate or dimolybdate and ferric nitrate.

In the preparation of the aqueous solution of the iron and molybdenum salts it is preferable to add complexing agents, such as citric, tartaric, malic or lactic acid, to avoid precipitation.

Generally the aqueous solution contains about 10–15% by weight of molybdenum salt and about 10–15% by weight of iron salt. Obviously, the relative amounts of the two salts are chosen as a function of the desired ratio between molybdenum oxide and iron oxide in the catalyst.

The support is then impregnated with the solution. To this end it is preferable to spray the solution in the form of very minute droplets on the granules of support which are kept under agitation, for example in a rotating apparatus. The impregnation may be carried out at room temperature or at a higher temperature, in a medium maintained at atmospheric or subatmospheric pressure. The quantity of solution used for impregnating the support is obviously dependent on the amount of iron and molybdenum oxides which it is desired to apply on the support.

The impregnated support is then dried at a temperature not exceeding about 120° C., and the dried support is calcined in an oxidizing atmosphere (such as air), generally for a period of about 5–15 hours. In a preferred embodiment calcination is first carried out at temperatures of the order of 300°–400° C. and generally for about 1 hour, maintaining the particles under fluidized conditions with air. Calcining is then completed at a temperature of about 400°–450° C. and generally for about 12 hours, maintaining the particles at rest and under a weak stream of air.

The catalyst of the invention is useful for the oxidation of methanol into formaldehyde by means of the fluidized bed technique.

More particularly, a gaseous stream containing methanol (generally from 4 to 6.5% in volume) and oxygen (generally from 10 to 20% in volume), the remaining percentage consisting essentially of inert gases, such as nitrogen, is introduced at the bottom of the fluidized bed. The reaction is carried out at a temperature of from 270° to 380° C. and with a contact time of at least 20 seconds and generally from 25 to 35 seconds. The minimum linear velocity of the gaseous stream necessary to obtain fluidization is of the order of 1 cm/sec. and the best fluidization conditions are obtained with linear velocities of the gas of the order of 4.5 cm./sec., and measured at the operating temperature and with an empty reactor.

The gaseous stream containing formaldehyde is recovered at the upper end of the reactor. This gaseous stream may be scrubbed with water to recover aqueous formaldehyde, or may be used as it is according to known methods.

In each case practically complete conversions of the methanol are obtained with high selectivities for the formaldehyde produced, as will be shown in the following experimental examples.

EXAMPLE 1

4.0 kg of microspheroidal silica having a surface area of 600 m$^2$/g, a density of 0.4 g/ml and a pore volume of 1 ml/g, are heated in air at 1,150° C. for 5 hours. The silica thus treated has a surface area of about 1 m$^2$/g, a density of 1.0 g/ml and a pore volume of 0.1 ml/g.

The 200–270 mesh fraction (53–74 microns) is then recovered by sieving, this fraction being the most suited for fluidization, given the characteristics conferred on the silica by heating. 1,400 g of this fraction are impregnated with 140 ml of a solution in deionized water containing 12.55 g of ammonium paramolybdate $((NH_4)_6Mo_7O_{24}.4H_2O)$, 13.0 g of ferric nitrate $(Fe(NO_3)_3.9H_2O)$ and 7.2 g of citric acid. Impregnation is carried out at ambient temperature by spraying the solution in the form of very minute droplets on the silica maintained under motion in a rotating flask which is kept at a residual pressure of 50–100 mmHg.

The impregnated particles are then dried up to 120° C., to confer some fluidity on the mass, and the latter is calcined by maintaining the particles under fluidization conditions in a stream of air, the temperature being brought to 360° C. in about 50 minutes. The product is then poured into a porcelain cup and calcining is completed by maintaining the cup for 12 hours at 420° C. in an oven in which a weak stream of air flows.

Upon cooling there is obtained a catalyst containing 0.88% by weight of iron and molybdenum oxides, based on the weight of silica, the atomic ratio between molybdenum and iron being equal to 2.2:1. The color of the catalyst is grey white and becomes pale green upon heating at 300° C.

EXAMPLE 2

4.0 kg of microspheroidal silica having a surface area of 580 m$^2$/g and a pore volume of 1 ml/g, are heated in air at 1,100° C. for three hours. The silica thus treated has a surface area of 58 m$^2$/g and a pore volume of 0.25 ml/g.

The silica is then impregnated with an aqueous solution of sodium carbonate, containing sodium in an amount corresponding to 0.2% by weight with respect to the silica. The impregnated silica is dried at 120° C. to remove the water and is then rapidly brought to a temperature of 750° C. The silica is maintained under such conditions for 5 hours, heated at 1,100° C. for 2 hours and then cooled. The silica thus treated has a surface area of 0.5 m$^2$/g, a density of 0.99 g/ml and a pore volume of 0.1 ml/g.

The silica is sieved to separate 900 g of the fraction having a size of from 53 to 74 microns. The catalyst is prepared by operating as in Example 1, the silica being impregnated with 110 ml of the solution described in said Example 1. The catalyst contains 1.1% by weight of iron and molybdenum oxides, based on the weight of silica, in a Mo/Fe atomic ratio of 2.2:1. The color of the catalyst is pale canary yellow and becomes brighter upon heating.

EXAMPLE 3

1,300 ml of the catalyst prepared in Example 1 are charged into a Pyrex tubular reactor having a length of 350 cm and an internal diameter of 39 mm.

A stream of air, to which methanol has been previously added in an amount equal to 6.2% in volume, is introduced at the bottom of the reactor at a rate of 125 N l/h. The catalytic bed thus fluidized has a height of about 155 cm.

The reaction is carried out at 320° C. with a linear velocity of the gaseous stream equal to 4.6 cm/sec. and with a contact time of about 39 seconds. Under these conditions the methanol conversion is 95% with a selectivity for formaldehyde equal to 90% with respect to the reacted methanol. The conversion and selectivity values are calculated in moles. The by-products of the reaction mainly consist of carbon oxides and water and contain small amounts of other compounds such as dimethyl ether and methyl formate.

EXAMPLE 4

1,200 ml of the catalyst prepared in Example 2 are charged into the reactor of Example 3. The operating conditions are the same as in Example 3, excepting the temperature which is kept at 350° C.

The methanol conversion is 92.2% with a selectivity for formaldehyde of 91.5%. Gas-chromatographic analysis of the gaseous stream issuing from the top of the reactor shows the following composition by weight: carbon monoxide 0.35%, formaldehyde 3.5%, dimethyl ether 0.15%, methyl formate 0.01%, carbon dioxide 0.01%.

EXAMPLE 5 (comparative)

Operating as in Example 1, a catalyst is prepared by using a microspheroidal silica having a surface area of 250 m$^2$/g and a pore volume of 0.3 ml/g.

The catalyst which contains 0.9% by weight of iron and molybdenum oxides, based on the weight of silica, in a Mo/Fe atomic ratio of 2.2:1, is charged into the reactor of Example 3. Air to which methanol has been added in an amount equal to 6.2% in volume is introduced at the bottom of the reactor at a rate of 150 N l/h. The catalytic bed thus fluidized has a height of about 230 cm. The reaction is carried out at 315° C. and with a contact time of 33 seconds, the other operating conditions being identical with those of Example 3.

The methanol conversion is 79% with a selectivity for formaldehyde of the order of 20%.

EXAMPLE 6

158 g of the catalyst prepared in Example 1 are charged into a Pyrex tubular reactor having a length of 1.0 meter and an internal diameter of 28 mm. Air to which methanol has been added in an amount of 6.2% in volume, is introduced at the bottom of the reactor at a velocity of 125 N l/h. Operating at 300° C. with a contact time of 3.5-4 seconds there is obtained a methanol conversion of 35% with a selectivity for formaldehyde of 89.5%.

EXAMPLE 7

A solution containing 12.55 g of ammonium paramolybdate in 100 ml of deionized water is prepared. 10.5 g of citric acid and 18.5 g of ferric nitrate are dissolved in the resulting solution. The solution is diluted to 140 ml by adding deionized water. 1,400 g of silica previously calcined and sieved as described in Example 1 are impregnated with the solution. Operating as in Example 1, there is obtained a catalyst which contains 1% by weight of iron and molybdenum oxides, based on the silica, the atomic ratio between molybdenum and iron being equal to 1.52:1.

The catalyst is used for the oxidation of methanol, at 320° C., the other operating conditions being the same as in Example 3. The methanol conversion is 92% with a selectivity for formaldehyde equal to 85%.

EXAMPLE 8

A catalyst is prepared by operating as in Example 1, using an alumina having a surface area of 1 m$^2$/g and a pore volume of 0.18 ml/g.

The catalyst which contains 0.9% by weight of iron and molybdenum oxides, based on the weight of alumina, in a Mo/Fe atomic ratio of 2.2:1, is then used for the oxidation of methanol at 300° C., the other operating conditions being the same as in Example 3. The methanol conversion is 95% and the selectivity for formaldehyde is 80%.

We claim:

1. A catalyst active and selective in the oxidation of methanol to formaldehyde and usable in the fluidized form in said oxidation, which consists essentially of iron and molybdenum oxides on a granular support, said support being a silica or an alumina having a specific surface area not exceeding 1 m$^2$/g and an overall pore volume not exceeding 0.2 ml/g and said oxides being present in the catalyst in an amount not exceeding 2 parts by weight for each 100 parts by weight of the support and in an atomic ratio between molybdenum and iron of from 1.5:1 to about 2.5:1.

2. The catalyst of claim 1, in which said support has a specific surface area of from 0.1 to 1 m$^2$/g and an overall pore volume of from 0.1 to 0.2 ml/g.

3. The catalyst of claim 1, in which said support is in the form of granules having a size of from 20 to 120 microns.

4. The catalyst of claim 1, in which said support is in the form of granules having a size of from 40 to 70 microns.

5. The catalyst of claim 1, in which the amount of said oxides is from 0.5 to 2 parts by weight for each 100 parts by weight of the support.

6. A method for preparing a supported catalyst active and selective in the oxidation of methanol to formaldehyde and usable in the fluidized form in said oxidation, which comprises:

(a) impregnating particles of silica or alumina having a specific surface area not exceeding 1 m$^2$/g and an overall pore volume not exceeding 0.2 ml/g, with an aqueous solution consisting essentially of decomposable salts of iron and molybdenum, the atomic ratio between molybdenum and iron in said solution being from 1.5:1 to 2.5:1 and the amount of solution being such as to ensure in the finished catalyst an overall content of iron and molybdenum (expressed as iron and molybdenum oxides)

not exceeding 2% by weight with respect to the weight of the support;

(b) drying the thus impregnated particles at a temperature not exceeding about 120° C.; and (c) calcining the thus dried particles at a temperature of from 300° to 500° C. in an oxidizing atmosphere, wherein the silica or aluminum in the supported catalyst exhibits said specific surface area and said overall pore volume.

7. The method of claim 6, in which the calcining of (c) is carried out for a period of from 5 to 15 hours.

8. The methods of claim 6, in which a two-step calcining is used in (c), the first step being carried out at a temperature of 300°-400° C. while maintaining the dried particles under fluidized conditions by means of a stream of air, and the second step being carried out at a temperature of 400°-450° C. with the particles at rest and under a weak stream of air.

9. The method of claim 6, wherein said specific surface area is from 0.1 to 1 $m^2/g$, said overall pore volume is from 0.1 to 0.2 ml/g and said overall content of iron and molybdenum is from 0.5 to 2% by weight with respect to the weight of the support.

10. The method of claim 6, wherein said aqueous solution further contains a complexing agent to avoid precipitation.

11. The method of claim 10, wherein said complexing agent is selected from the group consisting of citric, tartaric, maleic or lactic acid.

* * * * *